United States Patent [19]

Ward

[11] Patent Number: 4,807,177
[45] Date of Patent: Feb. 21, 1989

[54] MULTIPLE FORMAT HAND HELD LABEL PRINTER

[76] Inventor: Richard J. Ward, c/o Manhattan Electronics, 17 W. 45 St., New York, N.Y. 10036

[21] Appl. No.: 872,245

[22] Filed: Jun. 6, 1986

[51] Int. Cl.⁴ ............................................. G06F 15/21
[52] U.S. Cl. .................................. 364/900; 364/519; 364/403
[58] Field of Search .......................... 364/900 MS File

[56] References Cited

U.S. PATENT DOCUMENTS

| | | | |
|---|---|---|---|
| 4,189,337 | 2/1980 | Higgins et al. | 156/351 |
| 4,301,878 | 11/1981 | Soe | 364/466 |
| 4,439,257 | 3/1984 | Sato et al. | 156/64 |
| 4,516,208 | 5/1985 | Sakura et al. | 364/466 |
| 4,601,394 | 7/1986 | Hutner | 209/3.3 |
| 4,623,418 | 11/1986 | Gombrich et al. | 156/361 |
| 4,672,554 | 6/1987 | Ogaki | 364/479 |

Primary Examiner—Thomas M. Heckler
Assistant Examiner—Maria Napiorkowski
Attorney, Agent, or Firm—Natter & Natter

[57] ABSTRACT

A multiple format hand held label printer includes a processor, a memory, a keyboard, a thermal printer and an advance mechanism for a tape of successive labels carried on a substrate. The processor reads operator keyboard inputs and formats both machine readable bar code data and alphanumeric data for the printer. The printer is actuated to imprint such information on successive adhesive backed labels. In addition, the processor stores label print information and sequentially changes print indicia to meet particular requirements. The processor communicates with a system processor for coordinated inventory control, market study or other functions.

19 Claims, 5 Drawing Sheets

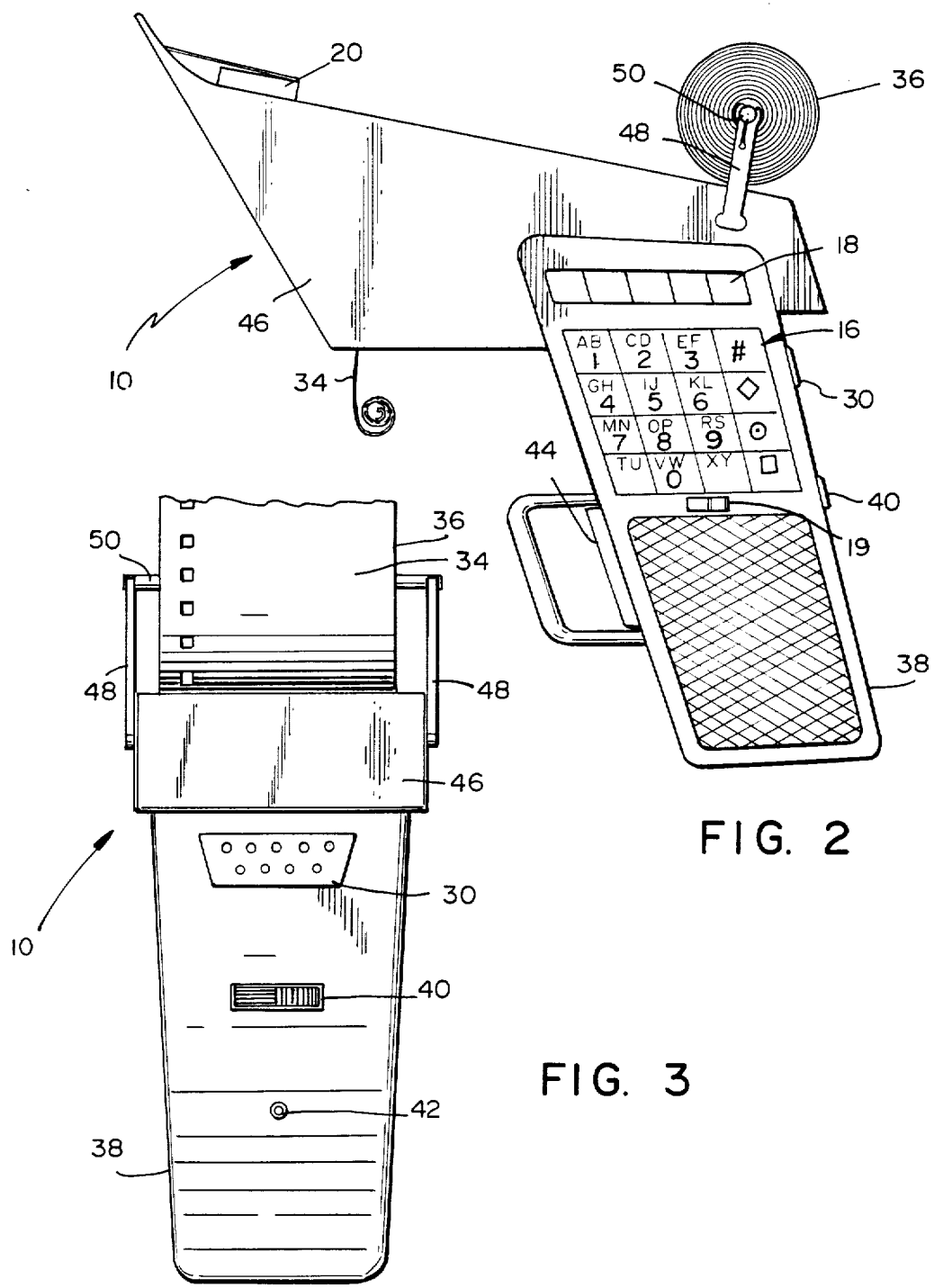

MULTIPLE FORMAT HAND HELD LABEL PRINTER

TECHNICAL FIELD

This invention relates generally to label printing devices and more particularly to a processor controlled portable label printing apparatus.

BACKGROUND ART

Adhesive backed price labels have been employed for many years in retail establishments for price marking goods. The advent of machine readable indicia such as UPC, EAN, JAN and WPC bar codes represented a significant advancement toward automating check out procedures and inventory control. Unfortunately, the implementation of manufacturer imprinted machine readable bar codes did not eliminate the necessity for merchants to mark products with human readable price indicia. Such requuirement was mandated by consumer interests in establishments which acquired check out systems incorporating bar code readers and was required, of course, in establishments which did not have bar code reading capabilities.

In addition, prior machine readable indicia was generally limited in scope to preprinted information and did not provide for individual establishment generated indicia and/or individualized data, as, for example, a sequential change in bar code indicia for assigning serial numbers in a production line or date coding otherwise identical merchandise. In the retail environment, individualized machine readable codes for inventory control, merchandise dating, individually weighed items, and the like could not be generated on a hand held portable label printer. The capacity to generate machine readable indicia in retail establishments for control of merchandise movement and the like was not available.

In view of the requirement to maintain the human readable pricing indicia on products at retail establishments, if machines readable indicia were custom imprinted upon a label for application to an article, a second separate label having alphanumeric pricing or other information was generally mandated. This, of course, entailed duplication of manual labor efforts as well as additional costs and possibilities for the introduction of errors.

SUMMARY OF THE INVENTION

A hand carried multiple format label printing apparatus includes a portable processor, a memory, a keyboard, a thermal printer, an advance mechanism for a tape of successive labels and a rechargeable power supply.

The user inputs both machine code and/or alphanumeric information into a keyboard which is read by the processor. The processor thereafter provides suitable signals to advance a tape carrying successive labels to a print head, printing signals for multiple format, i.e. machine code and alphanumeric, printing and signals to advance the tape from the printer to a substrate stripper and label applier.

The processor subroutine provides for automated sequential changes in printed indicia for data coding, serial number assignment or other information in machine readable format. Printed information as well as label count and other information are stored in memory. The stored data may be accessed by a system processor for coordination of applied labels with inventory records as well as other relevant data.

From the foregoing compendium, it well be appreciated that it is an aspect of the present invention to provide a portable head held label printing apparatus of the general character described which is not subject to the disadvantages of the background art aforementioned.

A feature of the present invention is to provide a portable hand held label printing apparatus of the general character described which imprints both machine readable code and human readable indicia on a single label.

A consideration of the present invention is to provide a portable hand held label printing apparatus of general character described which includes a memory for storage and retrieval of information relating to labels printed.

A further aspect of the present invention is to provide a portable hand held printing apparatus of the general character described which is capable of being economically manufactured by mass production fabrication techniques.

Another consideration of the present invention is to provide a portable hand held label printing apparatus of the general character described which is efficient in operation and capable of utilization by relatively unskilled workers.

An additional aspect of the present invention is to provide a portable hand held label printing apparatus of the general character described which is capable of interaction with a central processor for data processing.

Other aspects, features, and considerations of the invention in part will be obvious and in part will be pointed out hereinafter.

With these ends and view, the invention finds embodiment in certain combinations of elements in arrangements of parts by which the said considerations, aspects and features and certain other considerations, aspects and features are hereinafter attained, all as fully described with reference to the accompanying drawings and the scope of which is more particularly pointed out as indicated in the appended claims.

BRIEF DESCRIPTION OF THE DRAWINGS

In the accompanying drawings in which are shown some of the various exemplary embodiments of the invention.

FIG. 2 is a front elevational view of a typical hand held label printing apparatus in accordance with the invention and illustrating a coil of label tape mounted above a carriage, a hand grip including a keyboard for print data entry and a display;

FIG. 3 is an enlarged scale end view of the label printing apparatus and showing a jack for interfacing with the system processor;

DESCRIPTION OF THE PREFERRED EMBODIMENTS

The present invention provides a processor controlled hand held label printing apparatus. The processor functions to read operator keyboard inputs, to format both machine readable bar code and alphanumeric print indicia for a thermal printer, and to actuate the thermal printer for printing such information on successive adhesive backed labels. In addition, the processor stores label print information and sequentially changes print information to meet particular requirements. Further, the processor interacts with a system processor for coordinated inventory control, market study or other functions.

Figure 1:
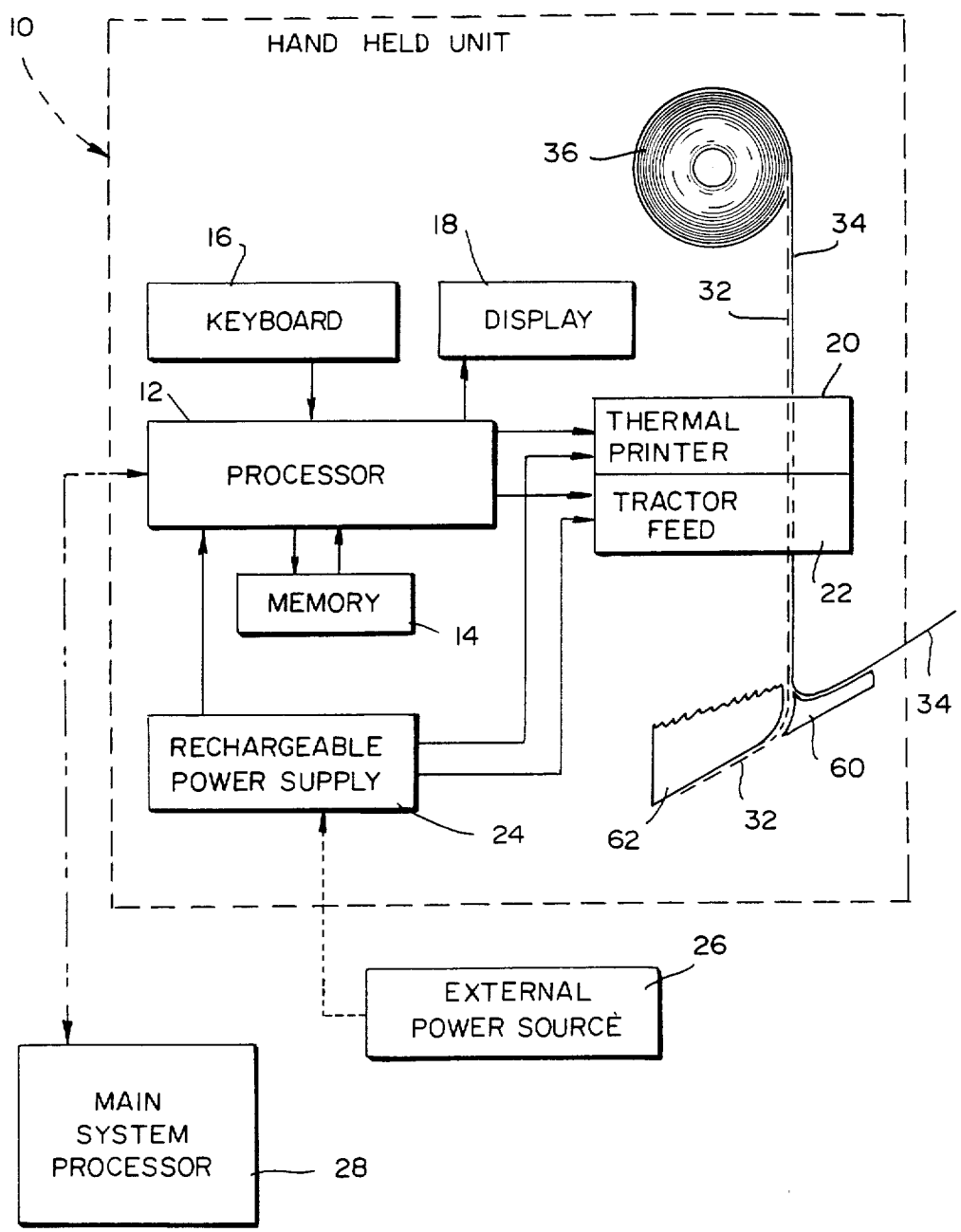
FIG. 1 is a schematized block diagram illustrating, in simplified format, a portable hand held label printing apparatus constructed in accordance with the present invention including a processor and depicting interaction of the processor with a system processor.

Referring now in detail to the drawings, a multiple format hand held label printing apparatus 10 constructed in accordance with and embodying the invention is illustrated in a typical configuration of a gun in FIGS. 2 and 3. It should be understood, however, that the particular shape of the printing apparatus is not significant. Accordingly, its housing or casing is illustrated with dashed lines in FIG. 1. FIGS. 1, 2 and 3 are the only FIGS. illustrating the apparatus 10 in its entirety.

With reference to FIG. 1 wherein components are illustrated in block format, it will be seen that the printing apparatus 10 includes a processor 12 which controls the functional operation of the apparatus. Any of numerous available processors may be employed in conjunction with the present invention, for example, a Gould AMI S6801 single chip micro computer may be utilized. An auxiliary memory 14 is coupled to the processor 12 to provide sufficient memory capability for storage of print information and other purposes.

The processor 12 reads operator inputs at a keyboard 16. The apparatus additionally includes a display, 18 which illustrates keyboard input, user prompts, increment count and similar information. The keyboard 16 and display 18 are also illustrated in FIG. 2. The keyboard entered print information includes machine readable bar codes or like codes and alphanumeric data such as item identification, dates, price data and the like. Alphanumeric print data may be distinguished from machine readable print data by an appropriate key, a sequence of keys or an optional selector switch 19 shown in FIG. 2. Such print information is formatted by the processor 12 for printing by a thermal printer 20 illustrated in FIGS. 1 and 5. If, for example, date coding is desired by only for market study purposes, or sequential serial numbers are not to be observed by prospective purchasers, such information is imprinted only in machine readable code.

Figure 4:
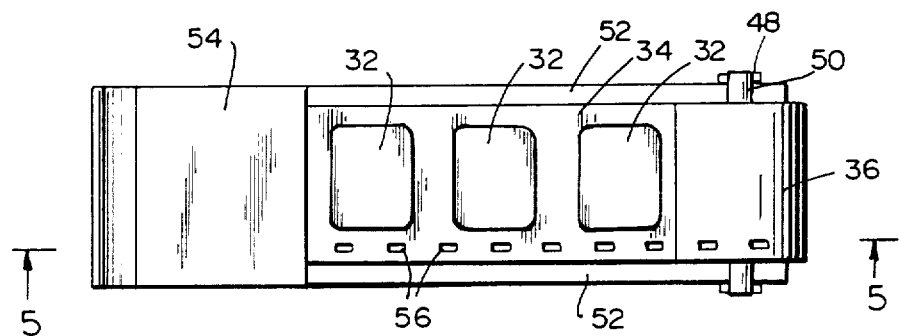
FIG. 4 is a top plan view of the label printing apparatus illustrating the carriage and showing a feed path of the tape to a thermal print head.
Figure 5:
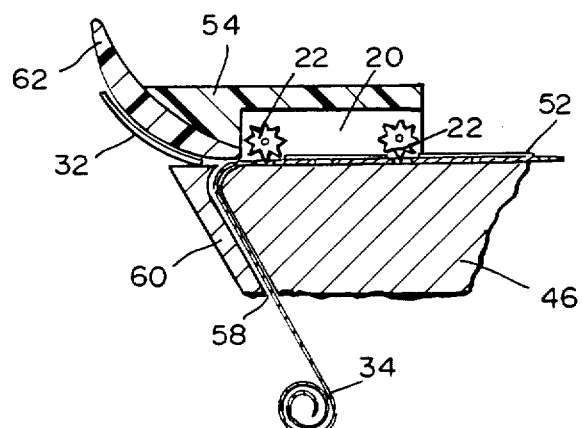
FIG. 5 is a fragmentary sectional view through the carriage, the same being taken substantially along the line 5—5 of FIG. 4 and showing the thermal printer, a tractor feed for the label tape, a tape substrate stripper and a label applying surface.

The printer 20 may incorporate, or the apparatus may employ, a separate tape feed such as a tractor or friction wheel feed 22 illustrated in FIGS. 1 and 5. To provide portability to the apparatus 10, an internal rechargable power supply 24 is included. The power supply is selectively recharged by coupling to an external power source 26. The hand held lable printing apparatus 10 utilizes the thermal printer 20 for the purpose of imprinting successive adhesive backed labels 32 initially mounted to a continuous substrate 34 of a coiled label tape 36. The labels 32, substrate 34 and tape 36 are illustrated in FIGS. 1 through 5.

In accordance with the invention, not only does the processor 12 store print information such as the data printed on each successive label but, in addition, a label count and successive incremental changes in each label and dating information such as the date the label was applied to the goods. The processor 12 interacts with a main system processor 28. The system processor 28 is selectively coupled to the processor 12 through a conventional interface such as an RS 232 interface through a suitable jack 30 illustrated in FIG. 3. With the system processor 28 interfacing the processor 12, print data stored in the processor internal memory or the memory 14 can be unloaded into memories associated with the main system processor. Thus inventory control, market surveys or other functions of the system processor are coordinated with printed labels which have been applied to goods. In addition, the interface between the system processor 28 and the processor 12 may be utilized to input label print data to the processor 12. In such instance a source of error in keyboard entry is avoided.

Turning now to FIGS. 2 and 3, it will be seen that in a typical configuration, the hand held label printing apparatus is shaped as a gun and includes a hand grip 38 having the alphanumeric keyboard 16 mounted thereon. In addition, the display 18 may be mounted to the hand grip 38. At the rear of the hand grip, a suitable power switch 40 may be positioned. Alternately, the power on/off function may be incorporated in one of the keys of the keyboard 16. Additionally positioned on the rear of the hand grip is a jack 42 for coupling the external power source 26 to the rechargable power supply 24 both of which are illustrated in FIG. 1.

Positioned on the front of the hand grip 38 is a suitable trigger switch 44 which may be employed as a dual function, print/advance switch. The trigger switch 44 is optional, however, and signals for printing labels 32 and advancing the tape 36 can be provided from selected keys of the keyboard 16.

Mounted above the hand grip 38 is a carriage 46 which includes a bracket 48 having a spindle 50 mounting the coiled tape 36. As best illustrated in FIG. 4, the tape 36 carries a plurality of the adhesive backed labels 32 in evenly spaced positions secured to the substrate 34. The tape extends within a recessed axial track formed in the upper surface of the carriage 46 from the rear end toward the front of the carriage. A pair of spaced parallel ridges 52 extend along the upper edges of the carriage 46 and provide longitudinal borders for the track as illustrated in FIGS. 4 and 5.

The tape 36 passes beneath a print head of the thermal printer 20. The printer 20 is mounted adjacent the front of the carriage 46 as illustrated in FIG. 5. It should be noted that a protective cushion 54 may be positioned over the thermal printer 20. As previously mentioned, the thermal printer 20 includes a suitable feed 22 for the tape. Illustrated in FIG. 5 is a tractor feed 22. The tractor feed includes a pair of toothed wheels which engage a plurality of successive perforations 56 formed in the tape substrate 34. Rotation of the wheels advances the tape and the successive labels 32 to a print station beneath the print head. Optionally, the tape feed may comprise one or more friction wheels and the substrate 34 as shown in FIG. 5 neet not be perforated.

Forwardly of the thermal printer 20, the carriage 46 includes a depending slot 58 for discharge of the substrate 34. The top of the foreward edge of the slot 58 includes a substrate stripper 60 which serves to separate the substrate 34 from the labels 32 and to direct the non adhesive printed surface of the labels against a curved label applier 62.

Figure 6:
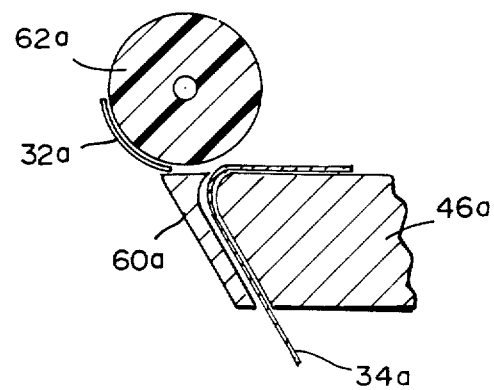
FIG. 6 is a fragmentary sectional view through the carriage and a label applying surface constructed in accordance with an alternate embodiment wherein the label applying surface comprises a roller.

In an alternate embodiment illustrated in FIG. 6, like numerals are employed to designate like components of the previous embodiment bearing, however, the suffix "a". An alternate label applier 62a is formed of a resilient roller. The remainder of the label printing apparatus is identical to the previous embodiment.

Figure 7:
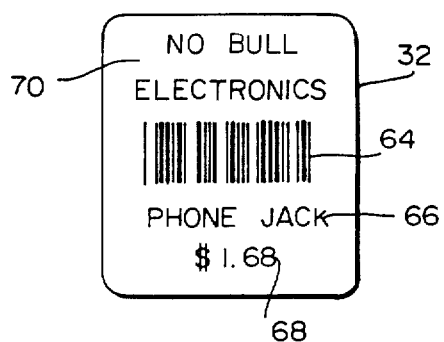
FIG. 7 is an enlarged scale plan view of a typical printer label showing both machine and human readable indicia printed thereon.

With reference now to FIG. 7 wherein a typical printed label 32 is illustrated, it will be seen that the thermal printer 20 is employed to imprint a machine readable code such as the code 64 and, in addition, alphanumeric information such as an item description 66 and price information 68. Additional alphanumeric information such as a store name 70 may be imprinted by the thermal printer 20 or may be preprinted on the labels by conventional printing techniques. It should also be appreciated that the bar code and alphanumeric information need not comprise pricing information but may include batch numbers, date codes, serial numbers, or any other information which may be desirable for market survey, research, identification or any other purpose.

Figure 8A:
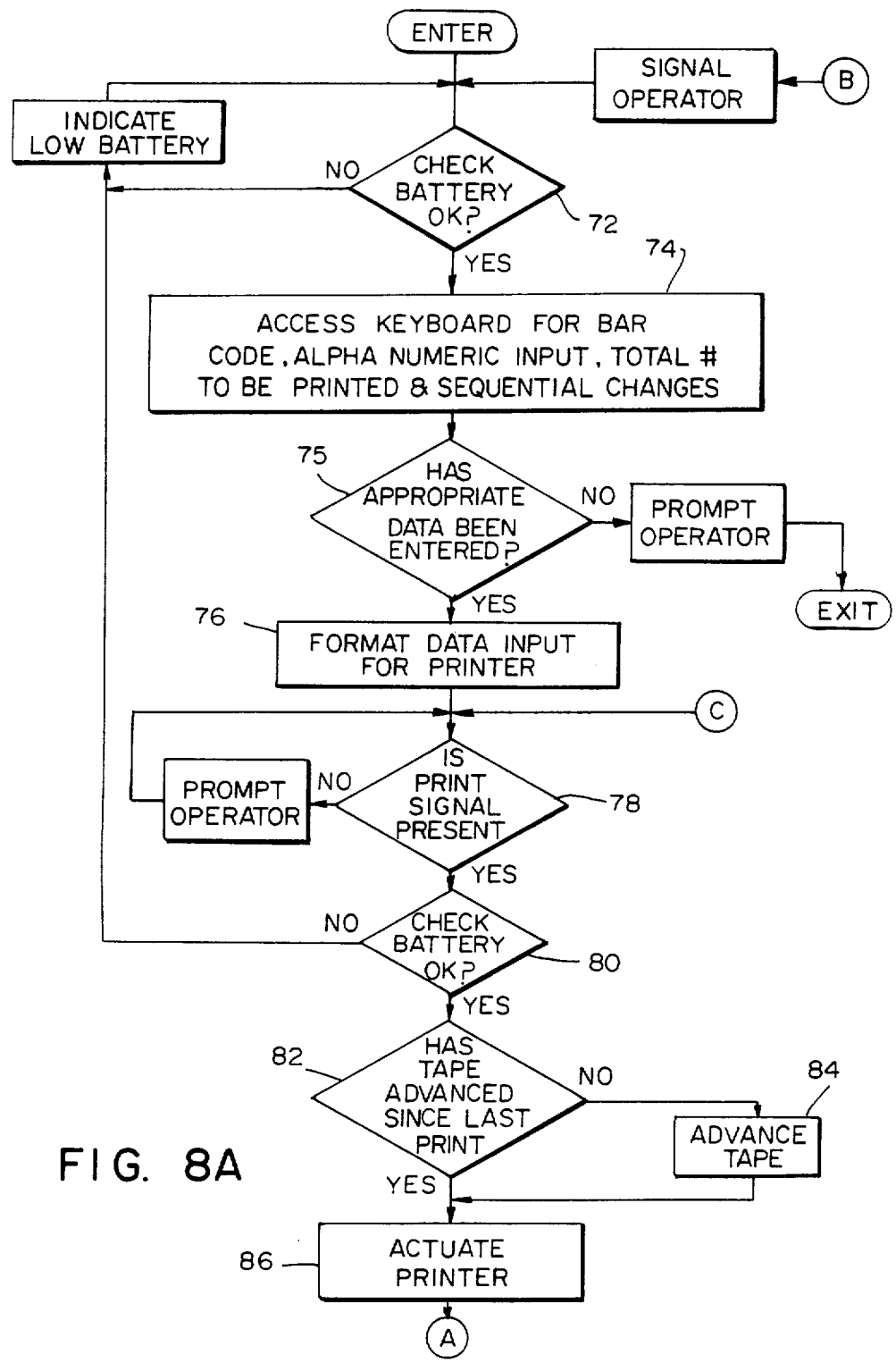
FIGS. 8A and 8B comprise a typical processor subroutine flow chart for inputting data to the processor and printing successive labels in accordance with the data input.
Figure 8B:
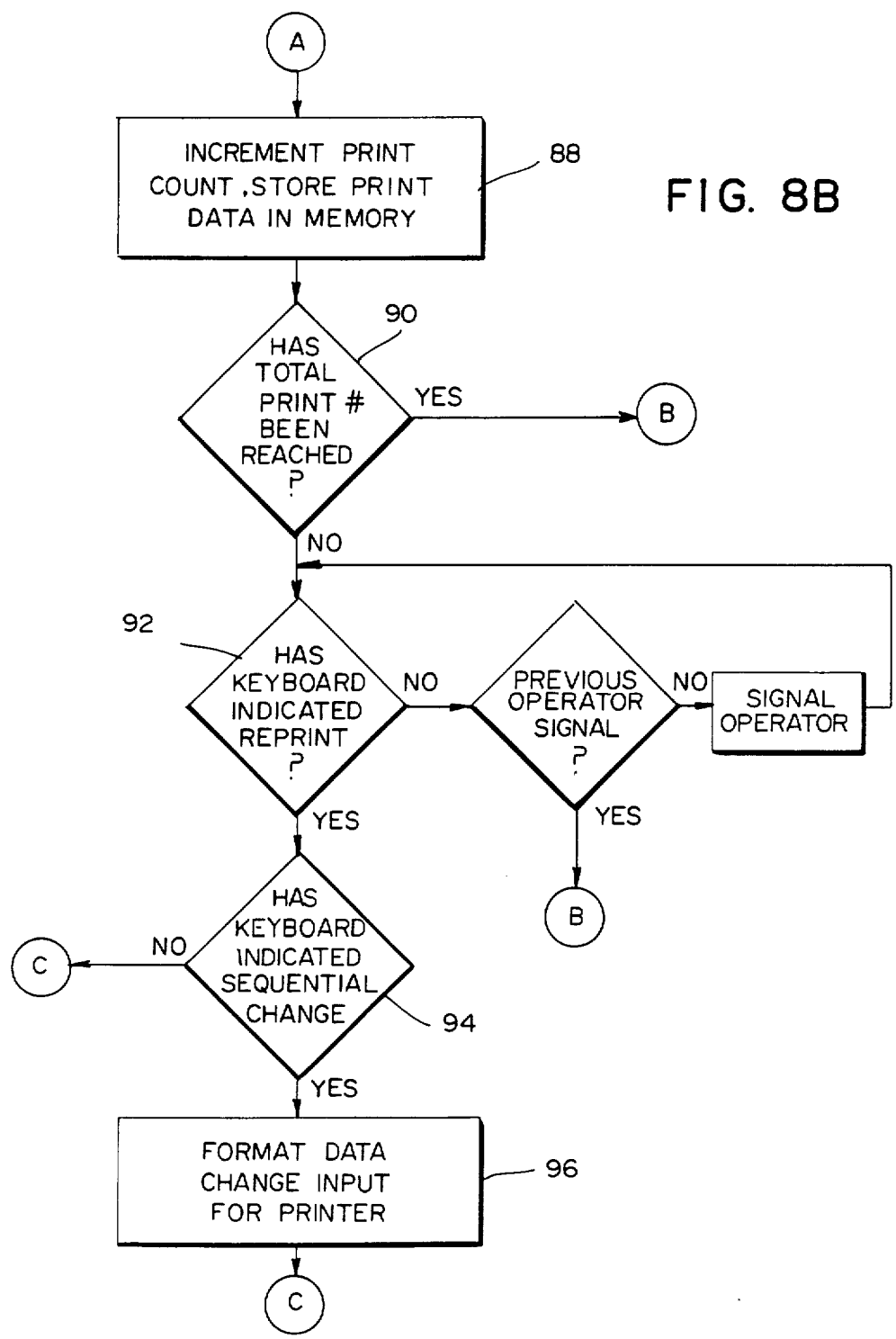

Turning now to FIGS. 8A and 8B wherein s typical subroutine for imprinting successive labels is illustrated, it will be seen that once the processor 16 has entered into a label printing subroutine, an initial battery check 72 is made to determine if the power supply is adequate for data processing, printing and related functions. Thereafter, the processor 12 accesses the keyboard 16 as illustrated in box 74 to obtaini the machine readable indicia, the alphanumeric indicia and any other indicia to be printed on the labels. Additional data obtained includes the total number of labels to be imprinted with the same or similar indicia and any sequential changes in either alphanumeric input or machine readable input for successive labels. An inquiry 75 is made as to whether appropriate data has been entered at the keyboard. If not, the operator is prompted and the processor exits the subroutine.

If appropriate keyboard entries have been made the processor 16 then formats the keyboard data input to generate signals suitable for the thermal printer 20 as indicated in box 76. An inquiry 78 is made as to whether a print signal is present. Such print signal may appear at the optional trigger switch 44 or at a selected key of the keyboard 16. If not signal is present, the operator is prompted visually or audibly and a further inquiry is made for the presence of a print signal.

Once a print signal is received, the battery status is again checked as indicated at 80 for verification that the power supply is sufficient to print, advance the tape and store printed information. If battery power is sufficient, a further inquiry 82 is made regarding whether or not the tape has been advance since the last printing. If not, the processor advances the tape by actuating the tape feed 22 as indicated at box 84 and then actuates the printer as indicated at box 86 to print both machine and human readable indicia.

After a label 32 has been printed, the processor 12 then increments the print count and stores the print data in a memory, for example, the memory 14 as indicated at box 88. Thereafter an inquiry 90 is made as to whether or not total number of labels to be printed has been reached. If the total number of labels to be printed has been reached, an operator signal is generated and the processor returns to the entry point. If the total number to be printed has not been reached, a further inquiry 92 is made as to whether or not the operator has indicated reprinting, if there has been no indication of reprinting, the operator is signaled after determining whether a previous operator signal has been made. In the event the operator has previously been signaled as to the lack of reprint instruction, the processor returns to the entry point.

If reprint has been indicated at the keyboard 16, an inquiry 94 is made as to whether or not the operator has indicated sequential change in data for successive labels. If a sequential change of data has not been indicated, the processor returns to the prior subroutine portion commencing with the inquiry 78 as to the presence of a print signal. If the operator did indicate a sequential change in print information, the processor formats the data change for inputting to the printer as indicated at box 96 and returns to that portion of the subroutine commencing with the inquiry 78 as to the presence of a print signal.

Thus it will be seen that there is provided a multiple format portable hand held label printing apparatus which achieves the various features, aspects and considerations of the present invention and which is well adapted to meet the conditions of practical use.

The term alphanumeric is merely exemplary of human readable indicia, all recognizable shapes and symbols including pictograms, pictographs, and the like should be considered as being encompassed by this term.

As various changes might be in the invention as above set forth, it is to be understood that all matter herein described or shown in the accompanying drawings is to be interpreted as illustrative and not in a limiting sense.

Having thus described the invention there is claimed as new and desired to be secured by letters patent:

1. A multiple format hand held label printing apparatus, said apparatus comprising processing means, the processing means controlling functional operation of the apparatus, means for printing successive labels in machine readable format and alphanumeric format, the means for printing being operationally connected to the processing means, means for inputting data to the apparatus, the means for inputting data including a keyboard, means for operatively interconnecting the means for inputting data and the processing means, the processing means receiving the data from the means for inputting data and in response thereto, formatting the data for printing indicia in machine readable code format and alphanumeric format, the formatted data corresponding to at least a portion of the data received, the means for printing receiving such formatted data and in response thereto imprinting corresponding indicia in both machine readable code and alphanumeric format on each selected label.

2. A multiple format hand held label printing apparatus constructed in accordance with claim 1 wherein the means for inputting data further comprises means for distinguishing between machine readable format data and alphanumeric format data.

3. A multiple format hand held label printing apparatus constructed in accordance with claim 1 wherein the means for inutting data to the apparatus includes means interconnecting the processing means with an external system processor, the external system processor transmitting a data signal to the processing means.

4. A multiple format hand held lable printing apparatus constructed in accordance with claim 1 further including memory menas for storing data corresponding to the formatted data, means selectively operatively interconnecting the processing means and an external system processor, the memory means being accessed to obtain the stored data, the stored data being transmitted to the system processor.

5. A multiple format hand held label printing apparatus constructed in accordance with claim 1 further including a tape, the tape comprising a plurality of labels and an elongated substrate, the labels being carried on the substrate, the apparatus further including means for advancing the tape to register a selected label with the means for printing.

6. A multiple format hand held label printing apparatus constructed in accordance with claim 5 wherein the means for advancing the tape comprises a wheel engageable with the substrate.

7. A multiple format hand held label printing apparatus constructed in accordance with claim 6 wherein the wheel is toothed and the substrate includes a plurality of perforations, successive teeth of the wheel being engageable with successive perforations of the substrate to advance the tape.

8. A multiple format hand held label printing apparatus constructed in accordance with claim 5 wherein the labels include and adhesive backing, the adhesive backing of each label being in contact with the substrate, the apparatus further including means for stripping the substrate from successive labels.

9. A multiple format hand held label printing apparatus constructed in accordance with claim 5, the apparatus further including means forming a feed path for the tape, the feed path means including a track, the apparatus further including means for stripping the substrate from successive labels and means for applying labels to articles, the means for stripping being positioned forwardly, along the feed path, of the means for applying.

10. A multiple format hand held label printing apparatus constructed in accordance with claim 9 wherein the means for applying labels to articles comprises a roller.

11. A multiple format hand held label printing apparatus constructed in accordance with claim 1 wherein the means for printing comprises a thermal printer.

12. A multiple format hand held label printing apparatus constructed in accordance with claim 1 further including a rechargeable power supply, the apparatus being selectively interconnected to an external power source for restoration of the power supply.

13. A method of printing labels with the multiple format hand held label printing apparatus constructed in accordance with claim 1, said method comprising the steps of:

(a) accessing the means for inputting data to obtain input data comprising alphanumeric format data, machine readable format data, the number of labels to be printed and information relative to any sequential changes in successive labels;

(b) formatting at least a portion of the data for controlling the means for printing;

(c) transmitting the formatted data to the means for printing;

(d) printing a label with visable indicia in both machine readable bar code format and alphanumeric format by actuating the printer; and (e) incrementing a print count and storing printed information in a memory.

14. A method of printing labels in accordance with claim 13 further including the steps of:

(f) determining whether the number of labels required has been printed;

(g) determining whether the input data indicated sequential changes in successive labels and, if so;

(h) reformatting the data to indicate the required sequential change;

(i) transmitting the reformatted data to the means for printing; and (j) printing the next sequential label with visible indicia in machine readable format and alphanumeric format by actuating the printer.

15. A multiple format hand held label printing apparatus, said apparatus comprising processing means, the processing means controlling functional operation of the apparatus, means for printing successive labels in machine readable format and alphanumeric format, the means for printing being operationally connected to the processing means, means for inputting data to the apparatus, means for operatively interconnecting the means for inputting data and the processing means, the means for inputting data comprising means for interconnecting the processing means with an external system processor, the external system processor transmitting input data to the processing means, the processing means receiving the data from the means for inputting data and in response thereto, formatting the data for printing indicia in machine readable format and alphanumeric format, the formatted data corresponding to at least a portion of the data received, the means for printing receiving such formatted data and in response thereto imprinting corresponding indicia in machine readable and alphanumeric format on a selected label.

16. A multiple format hand held label printing apparatus, said apparatus comprising processing means, the processing means controlling functional operation of the apparatus, means for printing successive labels in machine readable format and alphanumeric format, the means for printing being operationally connected to the processing means, means for inputting data to the apparatus, means for operatively interconnecting the means for inputting data and the processing means, the processing means receiving the data from the means for inputting data and in response thereto, formatting the data for printing indicia in machine readable format and alphanumeric format, the formatted data corresponding to at least a portion of the data received, the means for printing receiving such formatted data and in response thereto imprinting corresponding indicia in machine readable and alphanumeric format on a selected label, memory means for storing data, the stored data comprising input data and label count data, means for selectively operatively interconnecting the processing means and an external system processor, means for accessing the memory means to obtain the stored data and means for transmitting the stored data to the system processor whereby printed label data is coordinated in an operating system.

17. A method of printing labels with the multiple format hand held label printing apparatus constructed in accordance with claim 15, said method comprising the steps of:
   (a) accessing the external system processor to obtain input data comprising alphanumeric format data, machine readable format data, the number of labels to be printed and information relative to any sequential changes in successive labels;
   (b) formatting at least a portion of the data for controlling the means for printing;
   (c) transmitting the formatted data to the means for printing;
   (d) printing a label with visable indicia in machine readable format and alphanumeric format by actuating the printer;
   (e) incrementing a print count and;
   (f) storing printed information in a memory.

18. A method of printing labels in accordance with claim 17 further including the step of:
   (g) transmitting the information stored in the memory to the system processor.

19. A method of printing labels in accordance with claim 13 further including the step of:
   (f) transmitting the information stored in the memory to an external system processor.

* * * * *